United States Patent
Harte et al.

(10) Patent No.: US 9,307,906 B2
(45) Date of Patent: Apr. 12, 2016

(54) MULTIMODAL AUTOMATED SENSORY TESTING SYSTEM

(75) Inventors: Steven E. Harte, Livonia, MI (US);
Grant H. Kruger, Ann Arbor, MI (US);
Daniel Clauw, Ann Arbor, MI (US)

(73) Assignee: The Regents Of The University Of Michigan, Ann Arbor, MI (US)

(*) Notice: Subject to any disclaimer, the term of this patent is extended or adjusted under 35 U.S.C. 154(b) by 728 days.

(21) Appl. No.: 12/896,331

(22) Filed: Oct. 1, 2010

(65) Prior Publication Data
US 2011/0082384 A1    Apr. 7, 2011

Related U.S. Application Data

(60) Provisional application No. 61/248,118, filed on Oct. 2, 2009.

(51) Int. Cl.
*A61B 19/00* (2006.01)
*A61B 5/00* (2006.01)

(52) U.S. Cl.
CPC .............. *A61B 5/0002* (2013.01); *A61B 5/0053* (2013.01); *A61B 5/4824* (2013.01); *A61B 5/4827* (2013.01)

(58) Field of Classification Search
CPC ... A61B 5/0053; A61B 5/4824; A61B 5/4827
USPC .................................................. 600/553, 557
See application file for complete search history.

(56) References Cited

U.S. PATENT DOCUMENTS

| 4,768,521 | A  |   | 9/1988  | Schiffman et al. |
|-----------|----|---|---------|------------------|
| 5,012,817 | A  |   | 5/1991  | Zeilinski et al. |
| 5,022,407 | A  | * | 6/1991  | Horch et al. ................... 600/552 |
| 6,416,480 | B1 | * | 7/2002  | Nenov ................. A61B 5/1106 600/557 |
| 7,854,703 | B2 | * | 12/2010 | Poisner ......................... 600/552 |
| 2006/0122542 | A1 | * | 6/2006 | Smith et al. ................... 600/557 |
| 2006/0129068 | A1 |   | 6/2006 | Makosinski et al. |
| 2006/0241666 | A1 | * | 10/2006 | Briggs et al. .................. 606/181 |
| 2011/0009769 | A1 | * | 1/2011  | Hagau et al. .................. 600/557 |

FOREIGN PATENT DOCUMENTS

| FR | 2723833 A1 | 3/1996 |
| JP | 07-255728  | 10/1995 |
| KR | 20020053985 A | 7/2002 |

OTHER PUBLICATIONS

Baguley et al., "Vaginal Algometer Development and Application of a Device to Monitor Vaginal Wall Pressure", 2003, 5sheets.
Edwards, et al., "Evaluation of Biomechanical Properties of Human Skin", Clinics in Dermatology, (1995), 6 sheets.
(Continued)

*Primary Examiner* — Linda Dvorak
*Assistant Examiner* — Emily Lloyd
(74) *Attorney, Agent, or Firm* — Harness, Dickey & Pierce, PLC

(57) ABSTRACT

A computer-controlled sensory testing system is disclosed that can be used to further pain research and aid in the clinical diagnosis and treatment of pain syndromes. The system includes actuators to deliver pressure/deformation (strain), auditory, olfactory, and other stimuli to a subject. The system includes software to control the delivery of the stimuli. The system is further operable to receive feedback regarding the stimuli received.

27 Claims, 8 Drawing Sheets

(56) References Cited

OTHER PUBLICATIONS

Emelianov et al., "Elasticity Imaging for Early Detection of Renal Pathology", 1995, 13sheets.

Humphrey, J.D., "Review Paper: Continuum Biomechanics of Soft Biological Tissues"; The Royal Society (2003), 44 sheets.

Iggo, A., "Cutaneous and Subcutaneous Sense Organs", 6 sheets, http://bmb.oxfordjournals.org at University of Michigan on Aug. 7, 2010.

International Search Report and Written Opinion mailed Apr. 27, 2011 for PCT/US2010/051131 claiming benefit of U.S. Appl. No. 12/896,331, filed Oct. 1, 2010.

Jia et al., "Two Dimensional Straining Imaging of Controlled Rabbit Hearts", 2009, 14sheets.

Johansson, et al., "Tactile sensibility in the human hand: relative and absolute densities of four types of mechanoreceptive units in glabrous skin", J. Physiol (1979), 18 sheets.

Johnson et al. "An Inexpensive Self Assembly Pressure Algometer" 1997, 3sheets.

Kim, "Vascular Intramural Strain Imaging Using Arterial Pressure Equalization", 2004, 11sheets.

Mazza, et al., "Nonlinear elastic-viscoplastic constitutive equations for aging facial tissues", Biomechan Model Mechanobio, (2005), 12 sheets.

Pailler-Mattei, et al., "Science Direct: In vivo measurements of the elastic mechanical properties of human skin by indentation tests", Medical Engineering & Physics, (2007), 8 sheets.

Perl, E.R., "Myelinated afferent fibres innervating the primate skin and their response to noxious stimuli", J. Physiol., (1968), 23 sheets.

Polianski, "Computer Controlled Pneumatic Pressure Algometry a New Technique for Quantitative Sensory Testing", 2001, 11sheets.

Shoemaker, et al., "A Constitutive Model for Two-Dimensional Soft Tissues and Its Application to Experimental Data", J. Biomechanics, (1986), vol. 19, No. 9, pp. 695-702.

Wagner, et al., "Validation of 3-D finite element human fingerpad model composed of anatomically accurate tissue layers", (Aug. 2010), 5 sheets.

Weitzel, "High Resolution Ultrasound Speckle Tracking May Detect Vascular Mechanical Wall", 2009, 6sheets.

Wu, et al., "Nonlinear and viscoelastic characteristics of skin under compression: experiment and analysis", Bio-Medical Materials and Engineering 13, (2003).

Xie, "Correspondence of Ultrasound Elasticity Imaging to Direct Mechanical Measurements", 2005, 9sheets.

Xie, "Staging Deep Venous Thrombosis Using Ultrasound Elasticity Imaging Animal Model", 2004, 12sheets.

Gescheider, George A., " Psychophysics, The Fundamentals"; Third Edition; 447 sheets; 1997.

Fung, Y.C.; "Biomechanics, Mechanical Properties of Living Tissues"; Second Edition; 581 sheets; 1993.

Parris, Winston, "Contemporary Issues in Chronic Pain Management"; Ch.9; 19 sheets; 1991.

Melzack, Ph.D., Ronald, "Pain Measurement and Assessment"; 18 sheets; 1983.

Supplementary European Search Report dated Aug. 23, 2013 for European Patent Application No. EP10821337.2 (PCT/US2010/51131 filed on Oct. 1, 2010 which claims the benefit of U.S. Appl. No. 12/896,331), 5 pages.

Patent Examination Report from the Australian Patent Office for Application No. 2010-300372 issued Dec. 16, 2013 (which application claims benefit of U.S. Appl. No. 12/896,331, filed Oct. 1, 2010), 3 pages.

* cited by examiner

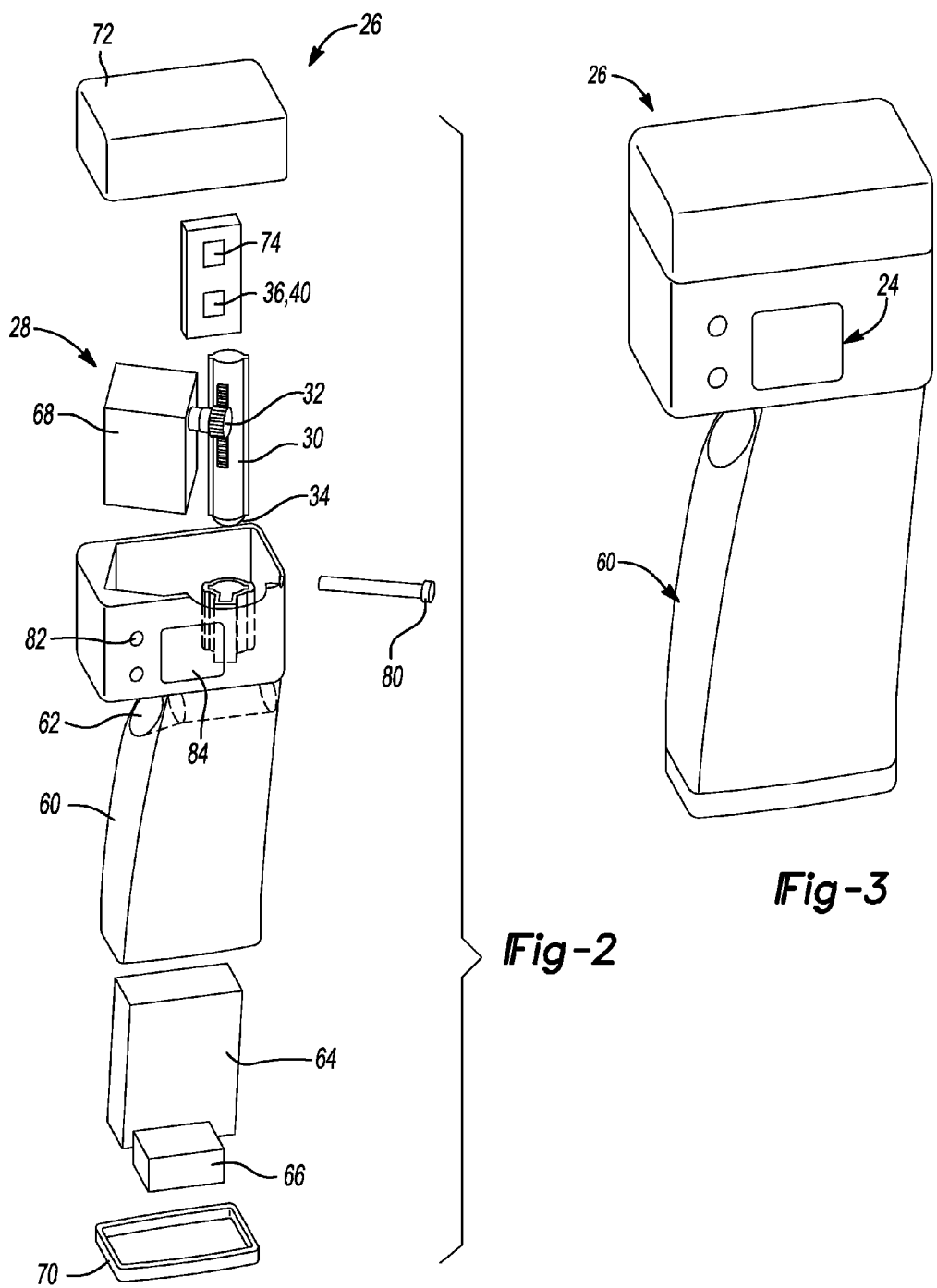

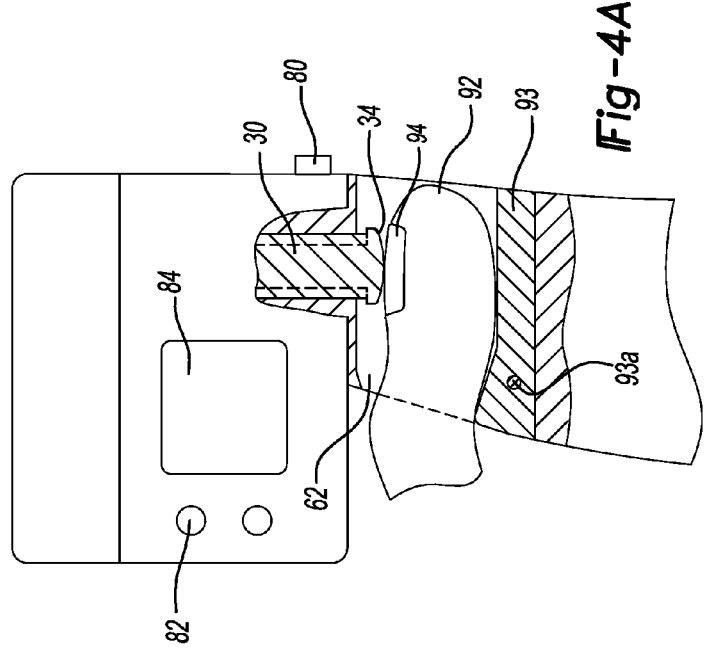
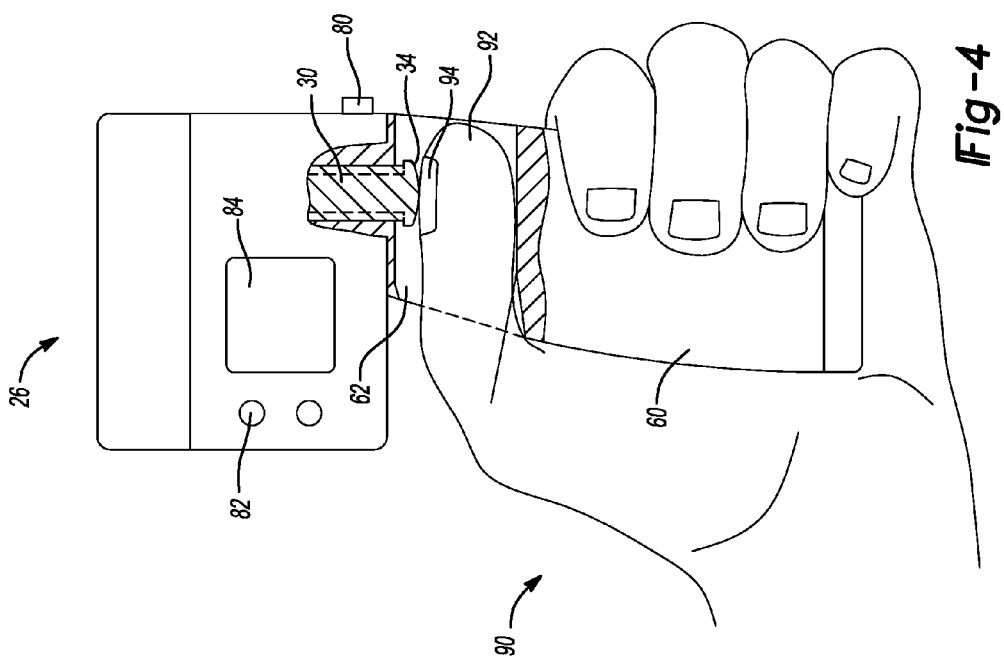

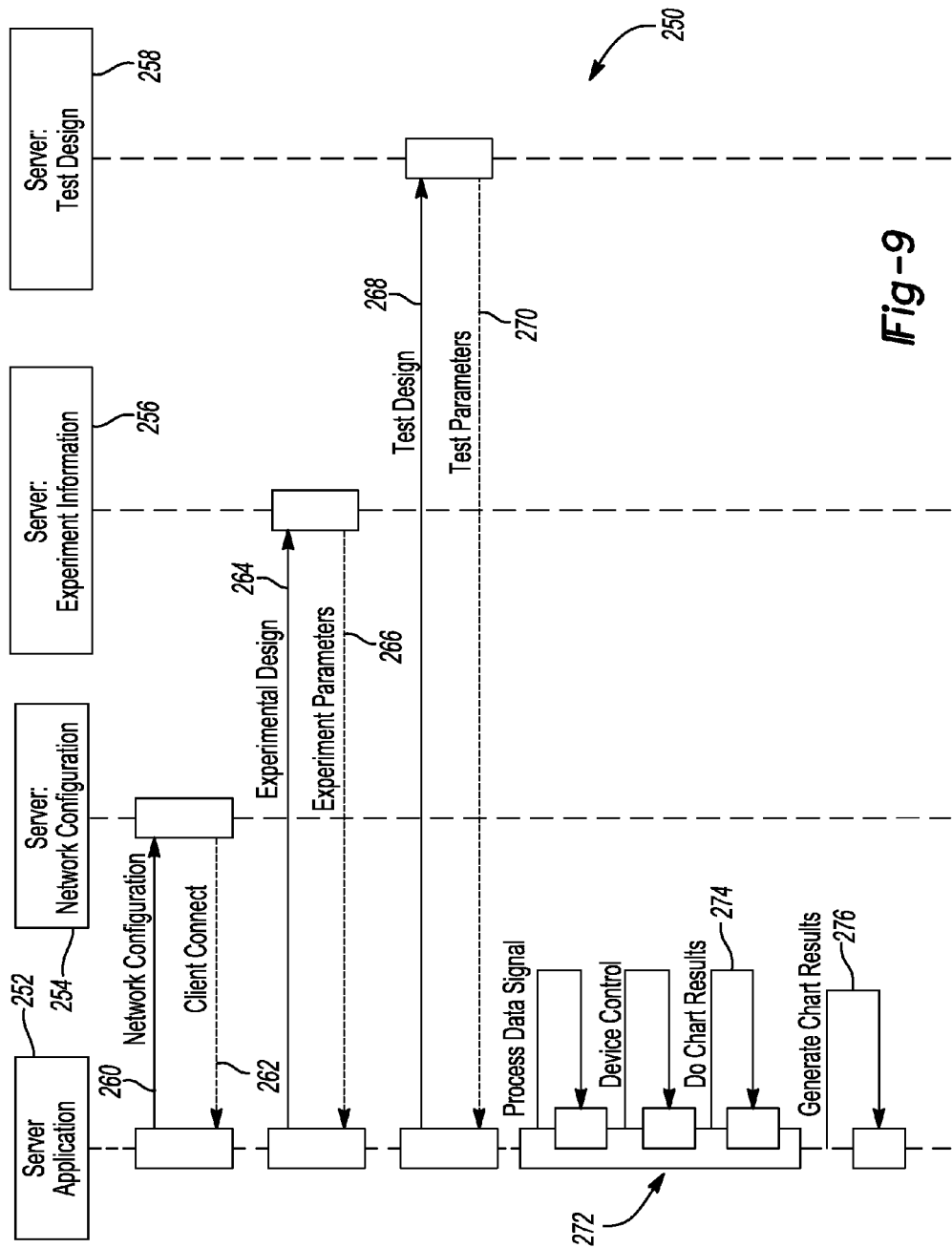

MULTIMODAL AUTOMATED SENSORY TESTING SYSTEM

CROSS-REFERENCE TO RELATED APPLICATIONS

This application claims the benefit of U.S. Provisional Application No. 61/248,118, filed on Oct. 2, 2009. The entire disclosure of the above application is incorporated herein by reference.

INTRODUCTION

The present technology relates to neurological diagnostic systems including methods and devices for monitoring and managing patient pain.

Physicians place an important role on patterns of pain in the diagnosis and management of their patients. Manual palpitation is a standard method of examination, but can have certain drawbacks, namely that the procedure is subjective and lacks the precision necessary to accurately assess, for example, the degree of inflammation of arthritic patients. The limitations of manual palpitation have been addressed by providing mechanical devices known as dolorimeters, algesiometers or algometers (the terms are used synonymously herein).

A dolorimeter is an instrument used to measure pain threshold and tolerance. Dolorimetry refers to the measurement of pain sensitivity or pain intensity. Several kinds of dolorimeters have been developed, including dolorimeters that apply pressure, heat, or electrical stimulation to some area, or move a joint or other body part and determine what level of heat, pressure, electric current, or amount of movement produces a sensation of pain. For example, pressure may be applied through pneumatic means using a blunt object, by locally increasing the pressure on some area of the body, or by pressing a sharp instrument against the body.

In the simplest form, a mechanical dolorimeter includes a simple spring loaded probe connected to a gauge. The gauge indicates the degree to which the spring within the probe is compressed, therefore the pressure exerted at the stimulation site can be determined. In use, the physician presses the probe against the portion of the patient's body where a pain measurement is to be made, and applies pressure until the patient feels discomfort. The reading of the gauge is noted, the reading being an indication of the degree of pain experienced at the measurement site, for example.

Typical dolorimeters and sensory testing devices often have one or more disadvantages that preclude them from being optimally useful in a clinical or research setting. For example, such devices typically only assess threshold and tolerance for a single sensory modality. In some cases, the device may be too simple to provide reproducible results; e.g., dolorimeters or palpometers that measure pressure pain threshold in a very rudimentary manner. Simple devices also typically do not compensate for perturbations from the experimenter, patient or subject, or the experimental or clinic process which can result poor quality data with high variability unrelated to sensory perception. Or, the device may be very operator dependent or too complicated to be used in clinical practice; e.g., heat pain threshold stimulators may require significant training and/or are not amenable for self-use by a patient. Streamlined and simplified devices and systems that can be used in a clinical setting and even operated in whole or in part by the patient would provide advantages.

SUMMARY

The present technology includes systems, methods, and devices that relate to measuring pain. Generally, the system includes a program or parameters that can be automatically carried out and applied to a patient with a stimulator. The automatic system can remove operator and patient variability. Also, the stimulators can be portable and repeatably used to obtain longitudinal and repeatability data and achieve confidence in change of patient response. Further, multiple stimulations can be simultaneously applied to a single patient and receive feedback regarding all forms and combination of stimulation. Communication regarding control and feedback can be wired or wireless.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is an exploded view of a stimulator system, according to various embodiments;

FIG. 3 is an assembled perspective view of the stimulator system of FIG. 2;

FIG. 4 is a partial cross-sectional environmental view of the assembled stimulator system of FIG. 3;

FIG. 4A is a is a partial cross-sectional environmental view of the assembled stimulator system of FIG. 3 showing an optional modular wedge;

FIG. 9 is a sequence diagram of an application to be used with the system illustrated in FIG. 8.

Corresponding reference numerals indicate corresponding parts throughout the several views of the drawings.

DETAILED DESCRIPTION

Figure 1:
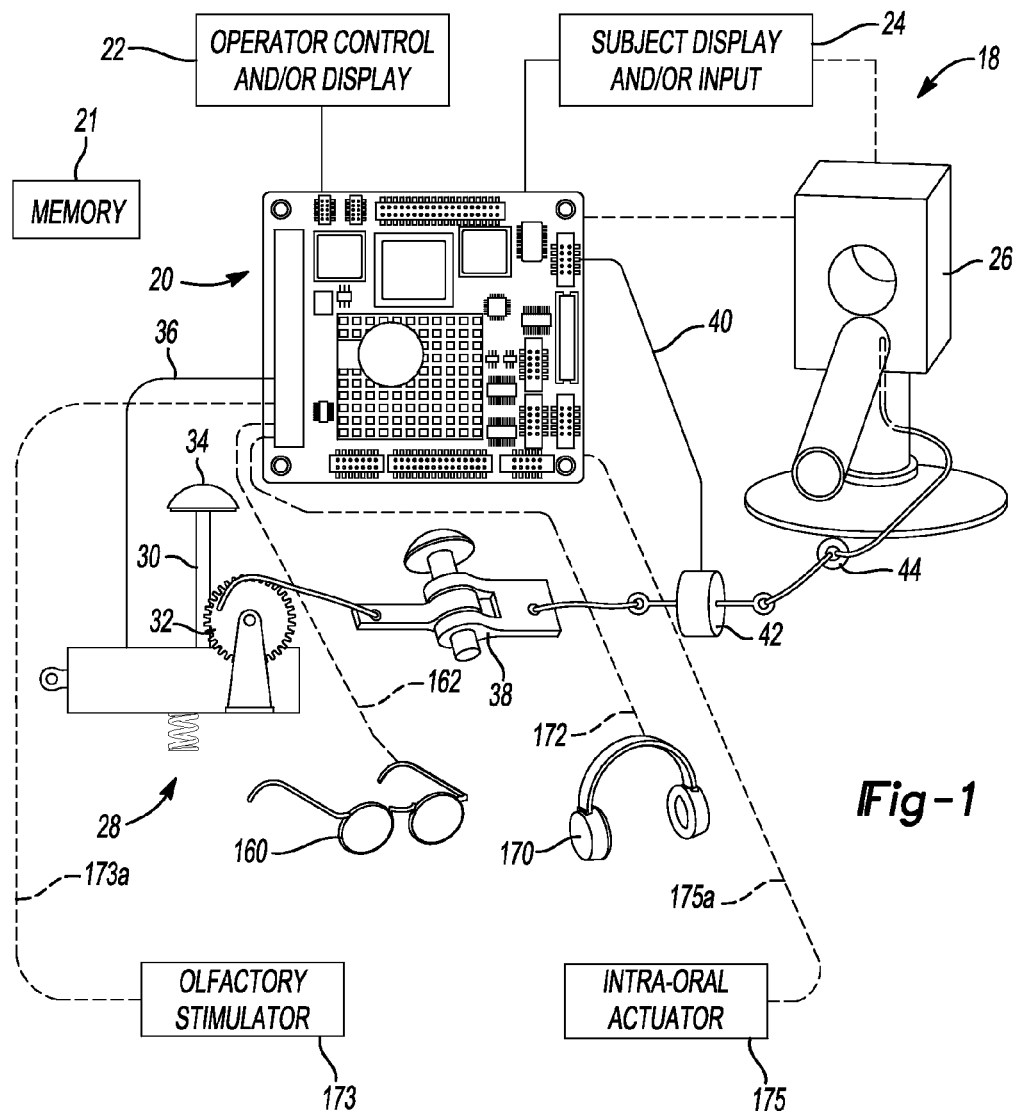
FIG. 1 is a schematic illustration of a Multimodal Automated Sensory Testing System.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references, including U.S. Patents and U.S. Patent Application Publications, cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

Overview

The present technology relates to a processor controlled, including a computer-controlled, multi-modal automated sensory testing (MAST) system 18, illustrated in FIG. 1, designed to further pain research and aid in the clinical diagnosis and treatment of acute and chronic pain. The system can include one or more actuators to deliver pressure, auditory stimuli, among other stimuli together or separately. Software can be provided to control and analyze data in real time or after data collection. The present system can include a wired or wirelessly distributed, quantitative sensory testing (QST) platform designed for research, clinical, and other applications. The system 18 facilitates the development of various algorithms, transducers, and testing protocols in order to further pain research and aid in the clinical diagnosis and treatment of pain syndromes.

Pain is a common symptom for which patients seek medical treatment and there is a need for standardized and objective methods for pain measurement. Some methods of quantifying pain are little more than lexicons for its verbal description or biomechanical methods for measuring the restriction of a particular range of motion or activities of daily living associated with the pain. Some psychometric methods attempt to quantify the personality or cognitive distortions from which the pain patient suffers. However, such methods do not reveal the covert and subjective sensory perception that is the pain experience in a way that can be quantified by an outside observer; for review, see Lipman J. J., Chapter 9: Pain Measurement In: Contemporary Issues in Pain Management. Parris, WCV (ed.) KLUWER Pubs., (1991).

It is from the general practitioner's office that referrals to neurologists and other pain specialists are made. For example, patient complaints of subjective numbness are often not detectable on clinical examination because present diagnostic methods are not sensitive enough to detect the early stage sensory impairments of such neurological disorders as nerve root entrapment or peripheral neuropathy. As a result, patients with these types of neurological disorders cannot be diagnosed or be easily diagnosed until the disorder progresses to a detectable level. The availability of a pain measurement device sensitive enough to detect the presence or absence of these and other abnormalities at an early stage may provide more effective medical intervention, or avoid unnecessary medical intervention. Such a device can be portable to increase cost-effectiveness, usability, flexibility, and/or save dedicated space for the practitioner and for clinical use as it should not require valuable dedicated space. Similarly, greater cost-effectiveness could be realized if the device were operable by a single person unaided or even operable by the subject or patient (used synonymously herein) him/herself.

Subjective pain perception does not bear a simple relationship to stimulus intensity, but it nevertheless has some quantifiable dimensions and limits: a lower level of identity (the pain threshold) and an upper level of identity (the tolerance level). Below the pain threshold, stimuli of increasing intensity destined to broach this level are perceived as non-painful (prepain). The pain threshold itself is highly labile and subject to psychological manipulation either of imposed suggestion (experimenter bias) or autosuggestion bias (the placebo response) or both. Pain threshold measurement procedures are generally believed to be unable to quantitatively demonstrate analgesic states engendered by clinically proven drugs as, for example, morphine (for review, see Chapman et al. "On the Relationship of Human Laboratory and Clinical Pain Research," Pain Measurement and Assessment, pp. 251-257 (Raven Press, New York, 1983)). Furthermore, the test subject, who may suffer excruciating pain of pathological origin, is less able to attend to the minor sensory nuances of the pain threshold.

An effective method for assessing the pain state of the patient and measuring changes in this state in response to treatment can be achieved with the MAST system 18. In some embodiments, the MAST system 18 is operable for objectively measuring pain. The system 18 generally includes a wired or wirelessly distributed, fixed or portable quantitative sensory testing (QST) platform designed for research, clinical, and other applications. The system facilitates the development of various algorithms, patient response scales, transducers and testing protocols in order to further and assist in pain research and aid in the clinical diagnosis and treatment of pain syndromes.

MAST System

In some embodiments and with reference to FIG. 1, the MAST system 18 features a central server or other central processor 20 that coordinates testing protocols and program execution. Operators are able to custom configure and/or select from a memory 21 a testing algorithm prior to testing (e.g. a program to be executed) and monitor and record test progress in addition to other experimental data in real-time and/or after completion with an operator control 22 and/or display. The memory 21 can be a server memory and the central processor 20 can be a server system. A wireless or wired client may include a patient input and/or display 24, such as a touch screen panel, displays sensory rating scales and requests patient feedback. A wireless or wired thumbnail stimulator 26 (which can be any or combinations of various embodiments discussed herein) serves as an actuator device to evoke pressure pain. The software, however, can be utilized with other methods of stimulation and patient feedback systems. For instance, auditory tones of various frequencies can be delivered via a wired or wireless headset 170 (e.g., Bluetooth® communication equipment) to evoke loudness discomfort levels. The system 18 can have wired and wireless local area network (LAN), wide area network (WAN), and personal area network (PAN), for example Bluetooth® communication equipment, capability for integrating local feedback from patients and coordinating large scale clinical studies. The system 18 also has the capability to control multiple transducers simultaneously, for example multiple force transducers, thus facilitating testing of endogenous control mechanisms (i.e., diffuse noxious inhibitory controls or DNIC). The software can be used to design a testing regime, execute the regime and collect the resulting data.

With continuing reference to FIG. 1, the MAST system 18 that includes the central processor 20 and the thumbnail stimulator 26, as schematically illustrated in FIG. 1, can house and include a mechanical stimulator (e.g. a motor and gear) system 28 including a rack 30 and pinion gear 32 to drive a thumbnail transducer or pressure application member (pressure member) 34. According to various embodiments, the motor and gear system 28 can be housed in the housing of the stimulator 26, as discussed further herein. The housing can further include a wired or wireless connection 36 with the central processor 20. The connection 36 with the central processor 20 can operate the motor and gear 28 according to the selected algorithm in the software but can also include transmission of data, including test results, pressure application, and other information to the central processor 20.

Provided on the housing or accessible by a patient or user is a kill or safety switch 38 to assist in safe operation of the thumbnail stimulator 26. In particular, at a selected time, such as when a user has reached an intolerable level of pain, the user or patient can activate the kill switch 38 to substantially immediately or quickly release pressure from the pressure application member 34. In addition, or alternatively to the kill switch, can be a manual or safety shaft that can remove the transducer from the subject after the test or at any selected time.

In addition to the communication connection 36, a second communication connection 40 can also be provided from a force or pressure sensor 42. The pressure sensor 42 is illustrated separate from the motor and gear assembly 28, but can be provided substantially integrally therewith. The force sensor 42 can sense the force applied through the pressure member 34, such as a deflection of the rack member 30, the transducer member 34, or other portions of the force application motor and gear system 28. For example, the force sensor can include a position/displacement or drive shaft angle transducer attached or positioned at a proper location relative to the transducer 34 to measure the position of the transducer 34 or subject strain (e.g. tissue strain as discussed herein) at the site of stimulation. In a further particular example, angle encoder can be attached to a shaft that drives the pinion 32 of the motor and gear assembly 28. The force sensor 42 can provide a signal that is transmitted to the central processor 20 with the connection 40.

The connection 40 can also be a wired or wireless connection. It will be further understood that the connections 36 and 40 can be a single connection and are illustrated separately for clarity of the current discussion. Additionally, a mechanical linkage can interconnect the motor and gear system 28 with the thumbnail stimulator 26 and a shear or safety ring or member 44 can be provided to ensure that only a maximum limited force is applied to the pressure member 34 to the patient undergoing the pain study.

The MAST system 18 can include, as the central processor 20, an appropriate microprocessor, such as an Intel Atom® 1.6 GHz processor. The memory 21 can include both random access memory and stable or hard drive memory. The processor 20 and the memory 21 can be incorporated in a computer, such as a workstation (e.g. a tablet, laptop, or desktop computer system), that has both wireless and wired network connections, a touch screen or non-touch screen display panel, and local wireless communication capability, such as a Bluetooth® communication equipment capability. In addition, the software of the MAST system 18 can be provided to operate on any appropriate operating system including Windows® based operating system, Apple® based operating system, Unix® operating system or Linux® operating system and compatible operating systems and the like.

The software can be accessed from the memory system 21 to provide instructions to be executed by the processor 20 for various test procedures to be carried out with stimulators, as discussed further herein. The test procedures can include rate and duration of application of force, peak force, incremental/discrete or continuous force application, inter-stimulus interval or other appropriate test procedure parameters. The test procedure can be completely stored in the memory system or can be altered in the system based upon a particular patient or subject by the system operator. Also, the software of the MAST system 18 can allow for self-regulation or change based on the stimulation and/or test sequence parameters in response to external variables, such as subject feedback or input or variant in geometry or other subject variables (e.g. geometry of the subject's digit).

Additionally, the test procedures encoded in the software, either regarding application of the testing or analyzing the results of the test, can take into account various patient attributes. For example, a chronic pain patient may have a lower pain threshold or pressure threshold that a non-chronic pain patient. This can be accounted for in analysis of the results of the test performed on the subject.

Additionally, tissue of the patient, including the skin of the patient, includes nerve receptors that can respond or be highly sensitive to mechanical deformation of skin. However, the deformation of the skin can be based upon various influences of the patient, such as genotype and/or phenotype of the patient, maturation or aging, skin diseases, environmental or hydration of the skin, and other patient specific or variability features.

Additionally, the various stimulators, as discussed herein, that can stimulate by application of pressure to skin or an overlayment of skin of the patient may also vary in deformation based upon resistance of the skin or overlayment. Accordingly, the stress and strain and the related stress-rates and strain-rates can be determined, such as by measuring, and controlled for the stimulators. Accordingly, the soft tissue of the skin can have a final strain that is a function of strain rate and time due to an applied stress, such as the stress applied with the stimulation device. Thus, monitoring the strain and analyzing the monitored strain can provide a dependent variable of stimulation while stress can be an independent variable of the stimulation system. For example, regarding digit of the patient, variations in nail hardness, thickness, geometry, as well as tissue elasticity and thickness and other physical or physiological variances can influence strain for any particular stress applied to the patient.

Figure 1A:
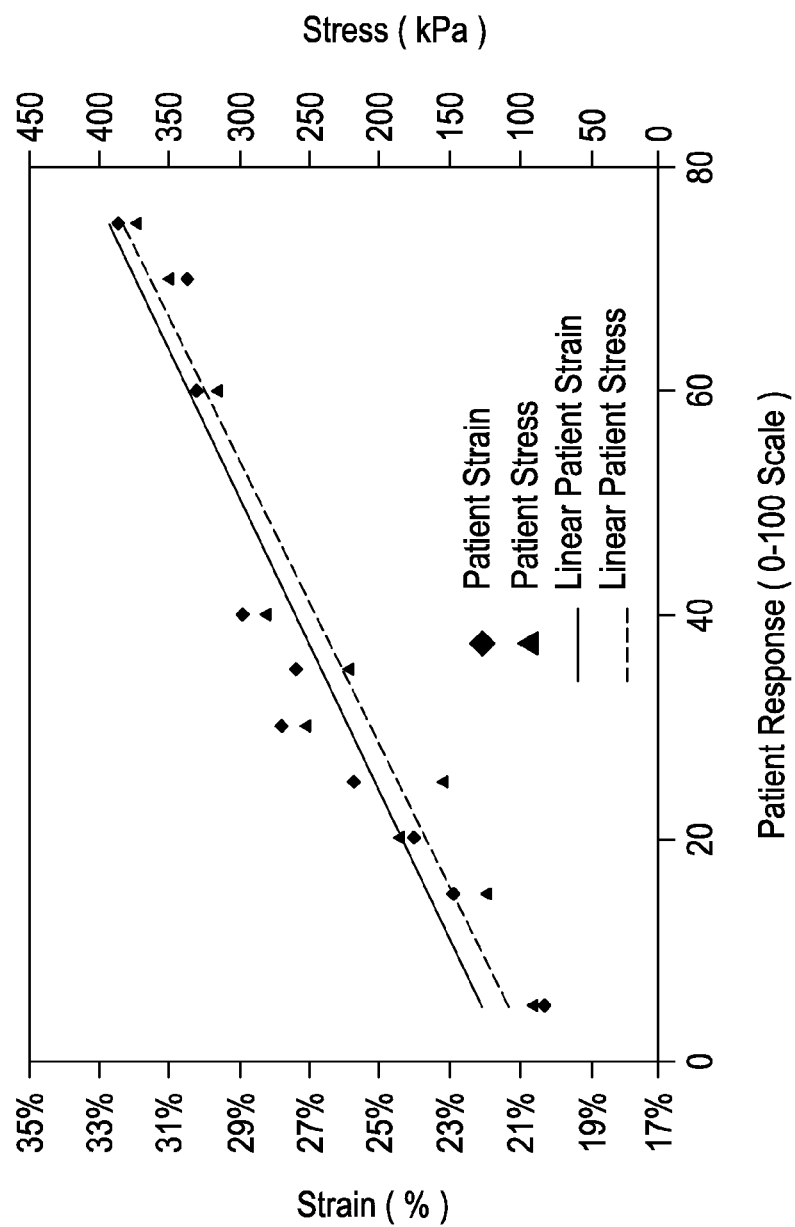
FIG. 1A is a graph of measured stress and strain plotted relative to subject pain.

Accordingly, measuring the strain and stress can assist in analyzing the results of the procedure including accounting for variances between different subjects and allowing for correlations to be determined while accounting for the variances. For example, a graph in FIG. 1A illustrates a plot and the related linear relationships of measured stress (in kilopascals on the right axis) and strain (percent of tissue deflection on the left axis) is plotted in relation to a patient or subject perceived pain response on a scale of 0-100 (bottom axis, where increasing values is increasing patient perceived pain). As illustrated, there is a relationship between the measured stress (force or pressure) and the measured strain (tissue deformation) versus the pain rating from the patient. Due to the relationship of the stress and strain, either can be used for measuring stimulus. Without being bound by the theory, however, stress is a response variable (because it relates to patient variability) while stress is an input variable as it is the applied force. In addition, by measuring the response variable of strain, variability amongst patients and stimulator devices may be accounted for. Thus, the software can analyze the results based on included instructions regarding the measured stress and strain to relate to the feedback from the subject regarding the applied stimulus, such as the onset of pain from the stimulator, according to various embodiments, such as the stimulator 26.

Digital Stimulators

In some embodiments, the pressure stimulator 26 applies a blunt force stimulus to the thumbnail bed, such as with the transducer member 34. The peak force and rate of application, or other features of the force versus time profile, which is set in the software, can be applied by the force application system of the motor and gear system 28 housed in a hand piece 60, as illustrated in FIG. 2. Accordingly, the gear and motor 28 and the stimulator 26, along with the kill switch 38 and the force sensor 42, can be incorporated into the hand piece 60 that is connected, as discussed herein, to a processor, including the central processor 20. In other words, the stimulator 26 shown in FIG. 2 can be used in the system schematically illustrated in FIG. 1. The hand piece module 60 is ergonomically designed to be held comfortably in either the left or right hand and maintain a thumb of a patient in a consistent position for testing, in a thumbhole 62.

The hand piece 60, illustrated in FIG. 2, can house the various components, as discussed above, and further herein. For example, the hand piece 60 can enclose or be formed to include a power source or power cell, such as a lithium ion rechargeable battery 64. The battery can include a 4 cell, 14.8V lithium polymer battery. A voltage regulator 66 to control the voltage to a DC motor 68 that is in turn connected to the pinion gear 32 and the rack 30 can also be provided in the housing 60. A bottom cover or base plate 70 can cover the bottom of the handle 60 while the top cover or top plate 72 can be provided to cover a top of the handle portion 60. Various connections, such as snap fits or adhesives can be used to connect the top cover 72 and the bottom cover 70 to the main handle 60.

The handle 60 can further house a communication system, such as a wireless communication system including a Bluetooth® transceiver system as the connections 36, 40. The thumbnail stimulator 26 can further house an internal processing system, such as a processor or controller 74 included on a circuit board with or separately from the connection system 36, 40.

Accordingly, the hand piece 60 can substantially enclose all of the portions necessary to apply a physical pressure to the patient. Also, the housing 60 can be ergonomically held in a single hand of the patient. The communication or connection systems 36, 40 can then connect to the central processor 20, such as a central server, for delivering pressure force to the patient according to the pre-designed or selected program algorithm. The central processor 20 can communicate with the handheld thumb stimulator 60 to send or receive control signals regarding a stimulation profile including time, rate of application of force, peak force, and other controlled parameters for the application of the stimulus or pressure to the patient.

The pressure member 34 can also be included within the handle unit 60 to extend from the rack 30. The pressure member (also referred to as transducer member or plunger) 34 can be formed from various materials to include different and selected stiffness, hardness, and diameters to apply selected forces to the patient. Additionally, different geometries of the pressure member 34 can be provided to apply pressure to the patient at selected configurations.

Additionally, the handle unit 60 can include a safety release knob 80 similar to the safety lever switch 38 and/or the manual release shaft discussed above that can allow for a substantially immediate removal of pressure or activation of the motor 68. Other control buttons 82, such as a start button or onset of pain input button, can be provided for subject input on the handle 60. In various embodiments, the buttons or other subject inputs directly on the handle 60 can be the subject input 24. The control processor 74 can include a start of stimulus command and an end stimulus command based upon the algorithm applied or to remove pressure in case a link with the central processor 20 is lost. Also, force, strain, and time safety thresholds can be included, which can, at the start of each stimulus, be automatically set slightly above the desired stimulus parameters. Should excessive force be measured for any reason, or the test continue for longer than expected, or maximum compressed thumb thickness is detected the current stimulus can be terminated and the transducer 34 can be immediately removed from the subject.

The central processor 20 can include or be connected with separate stimulators, such as heat stimulators, visual stimulators, olfactory stimulators, tactile stimulators, heart rate sensors, respiration rate sensors, and other sensors to stimulate the patient and/or receive information regarding the patient during the application of stimulation, such as during a study. It will be further understood that various sensors can be integrated with the handle device 60, such as a pulse rate monitor and/or pulse-oximeter included within the thumb hole 62 or otherwise configured with the handle portion 60.

By monitoring the application of force, correct placement of the digit, such as a thumb can be discerned to ensure good experimental results are obtained. The wireless connection architecture allows the pressure stimulator device 26 to be controlled from any device that can act as the central processor, include wireless capable (e.g., Bluetooth®) devices, such as laptops, cell phones or desktop PCs. Force is applied through the pressure member 34 by controlling the torque supplied by a DC servo-motor 68 and transferred to the pain transducer 34 through a high-ratio gearbox and converted into linear motion by the rack 30 and pinion 32 of the motor and gear system 28. The motor voltage, current, and speed are measured and used for feedback control of the applied force. The MAST system 18 also has provision to incorporate the load-cell 42 for direct measurement of the applied force. An embedded proportional-integral-derivative control system (PID controller) incorporates calibration curves (e.g. linear or non-linear) to ensure accurate and repeatable testing can be performed. Additionally, the controller parameters of the central processor 20 or the hand-held processor 74 can be tuned to customize the force stimulation profile, providing added flexibility for research applications. The parameters can be customized prior to the initiation of the test.

With continuing reference to FIG. 2, the thumb stimulator 26 can further the include activation or control buttons 82 on the device body 60 itself. The control buttons 82 can allow the patient undergoing the test to input information directly into the thumb stimulator device 60, such as onset of pain, beginning of the algorithm cycle, and other information. The control buttons 82 can be an addition to the safety release knob 80. Additionally, the buttons 82 can be provided in place of the release safety knob 80 to act as a kill switch for the thumb stimulator device 26. Additionally, a mechanical system, such as a thumb screw knob, can be provided to retract or move the rack 30 to remove pressure from the patient.

Additionally, a screen or readout portion 84 can be provided on the thumb stimulator device 26 to allow feedback or input directly from the patient. For example, the stimulator 26 can be stand alone without connection to the central processor 20. The local or handheld processor 74 can execute the program and the display 84 can output results.

With reference to FIG. 3, the thumb stimulator 26 according to various embodiments is illustrated in an assembled configuration. The assembled configuration in FIG. 3 is the thumb stimulator 26 illustrated in FIG. 2 including the main body 60 and the various other components illustrated therewith. With additional reference to FIG. 4, the thumb stimulator 26 is illustrated in use and as grasped around the main body 60 by a hand 90 of the patient or test subject. A thumb 92 of the patient can be placed in the thumb hole 62 and in a digit placement site and positioned below the force transducer pad 34 that is connected to the rack 30. The force transducer pad 34 can be of any appropriate shape, such as planar, curved, etc. Also, the thumbhole 62 can include or be provided with a modular wedge 93 that can be held in place with a pin 93a, as illustrated in FIG. 4A. The wedge 93 can assist in positioning the thumb 92 at a selected orientation relative to the transducer pad 34, such as to achieve a substantially perpendicular application of force to the thumb 92. Though, the pinion 32, the transducer pad 34 or other portions of the drive system can be provided to move the transducer pad in any selected direction relative to the thumb, such as laterally, angularly, axially, etc. Also, sensors can be provided to measure the amount of movement in any of the selected directions.

Upon application of a force, such as with the motor 68 discussed above, the force transducer 34 is compressed against a nail 94 of the subject or patient and force would be transmitted to the nail bed of the thumb 92. The thumb hole 62 can ensure a substantially repeatable placement of the thumb 92 within the thumb hole 62 and its position relative to the force transducer pad 34 as the thumb 92 is pressed against the placement site. As discussed above, the control processor 74 can control the motor 68, such as an h-bridge directly form the battery, to exert a force, rate of force, peak force, etc according to the algorithm transmitted to the thumb stimulator 26 from the central processor 20.

The patient whose hand 90 is associated with the thumb stimulator 26 can press a start button, or the system can be started by an operator, and the patient can enter data directly onto the hand held device, such as with the buttons 82, or onto a separate input such as the user display and/or input 24 discussed above. The communication unit, including the wired or wireless connections 36, 40, can receive or transmit data, including the instructions for the algorithm to apply force, and send information relating to the force applied, and other instructions or inputs from the thumb stimulator device 26. As discussed above, the load cell or force sensor 42 can be associated with the rack 30, the force transducer pad 34, or other appropriate portion of the thumb stimulator device 26 to provide a substantially direct force measurement. The force measurement can be transmitted to the central processor 20 with the communication connections 36, 40 which can be both wired or wireless, according to various embodiments.

Figure 5:
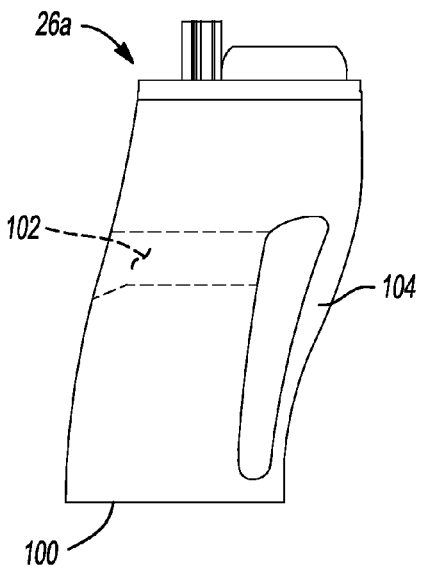
FIG. 5 is an assembled perspective view of a stimulator system, according to various embodiments.
Figure 6A:
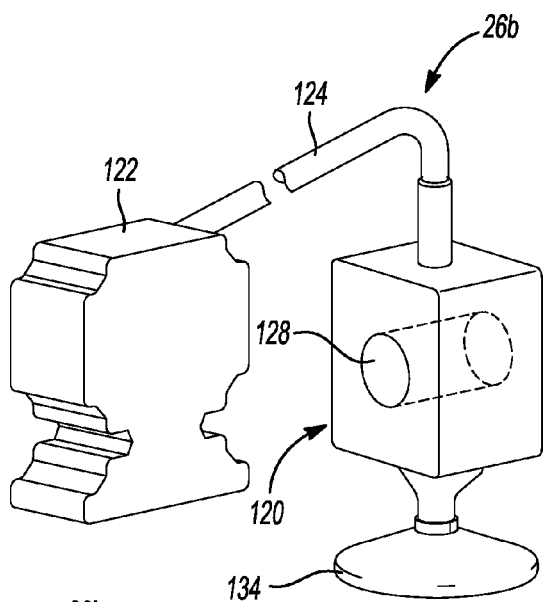
FIG. 6A is an assembled perspective view of a stimulator system, according to various embodiments.
Figure 6B:
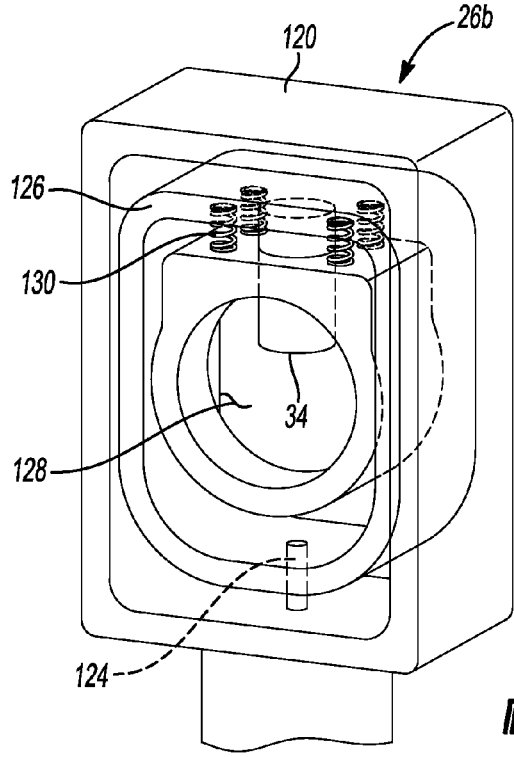
FIG. 6B is a partial cross-sectional environmental view of the assembled stimulator system of FIG. 6A.

It will be understood that the thumb stimulator 26 can be provided in various embodiments, including those illustrated further herein. For example, as illustrated in FIG. 5, a thumb stimulator 26a is illustrated. The thumb stimulator 26a, the motor and gear system 28, as discussed above in relation to the thumb stimulator 26 and generally in the schematic of the MAST system 18 in FIG. 1, can be incorporated into a hand held housing 100 that can define a thumb hole and/or wall 102 and also a finger or digits enclosing portion 104. The enclosing portion 104 can assist in grasping the housing 100, particularly for patients with weak grasp or other infirmities. Additionally, the digit holding portion 104 can be used particularly for pediatric patients that have a weaker grasp or smaller digits and may need assistance in holding the body 100. Additionally, the body 100, or the body of any of the illustrated or discussed embodiments, can be proportioned for various size patients. For example, small, medium and large bodies can be provided for pediatric patients, large patients, or patients with limited range motion, such as arthritic patients. Additionally, the body 100 can be provided without the digit capturing portion 104, but maintaining the other geometric designs of the body portion 100. Additionally, the various contours of the body portion 100 can be rounded, angular, or any appropriate geometric shape to be grasped by a user or patient during a testing procedure.

According to various additional embodiments, a thumb stimulator 26b is illustrated. The thumb stimulator 26b can be provided in various configurations, including a thumb stimulator holder or housing 120 that is separate from a motor housing 122. The motor housing 122 can include a motor, such as the motor discussed above, that transmits a force through a cable 124 to a lever 126 within the thumb holder housing 120. The force transducer pad 34 can be included within the thumb holder housing 120 to pass into a thumb hole 128 and be engaged by the lever 126. The cable 124 can attach the lever 126 to apply a force to overcome a spring or resilient member 130 to move the transducer pad 34 towards the thumb 92 positioned within thumb hole 128. Accordingly, a rack and pinion system, including that discussed above, is not necessary to move the force transducer pad 34 against the thumb 92 of the patient. However, the various control and communication systems can be provided in or coupled to the thumb stimulator 26b to allow for control of the application of force and for input from both a patient and an operator.

It will also be understood that the motor housing 122 and the thumb holder housing 120 can be incorporated into a single assembly, similar to that illustrated on the assembly 26.

Nevertheless, it may be selected to separate the drive system from the thumb holder housing 120 for various applications. For example, the thumb holder housing 120 can be mounted with a vacuum pad 134 to a desk or base that is substantially transportable, but holds the thumb holder housing 120 in a selected position for the duration of a test. It will be understood, that the vacuum pad 134 can also be incorporated or included with the thumb stimulators according to any appropriate embodiments, including those discussed above, in addition to or alternatively to other holding or mounting mechanisms.

Figure 7:
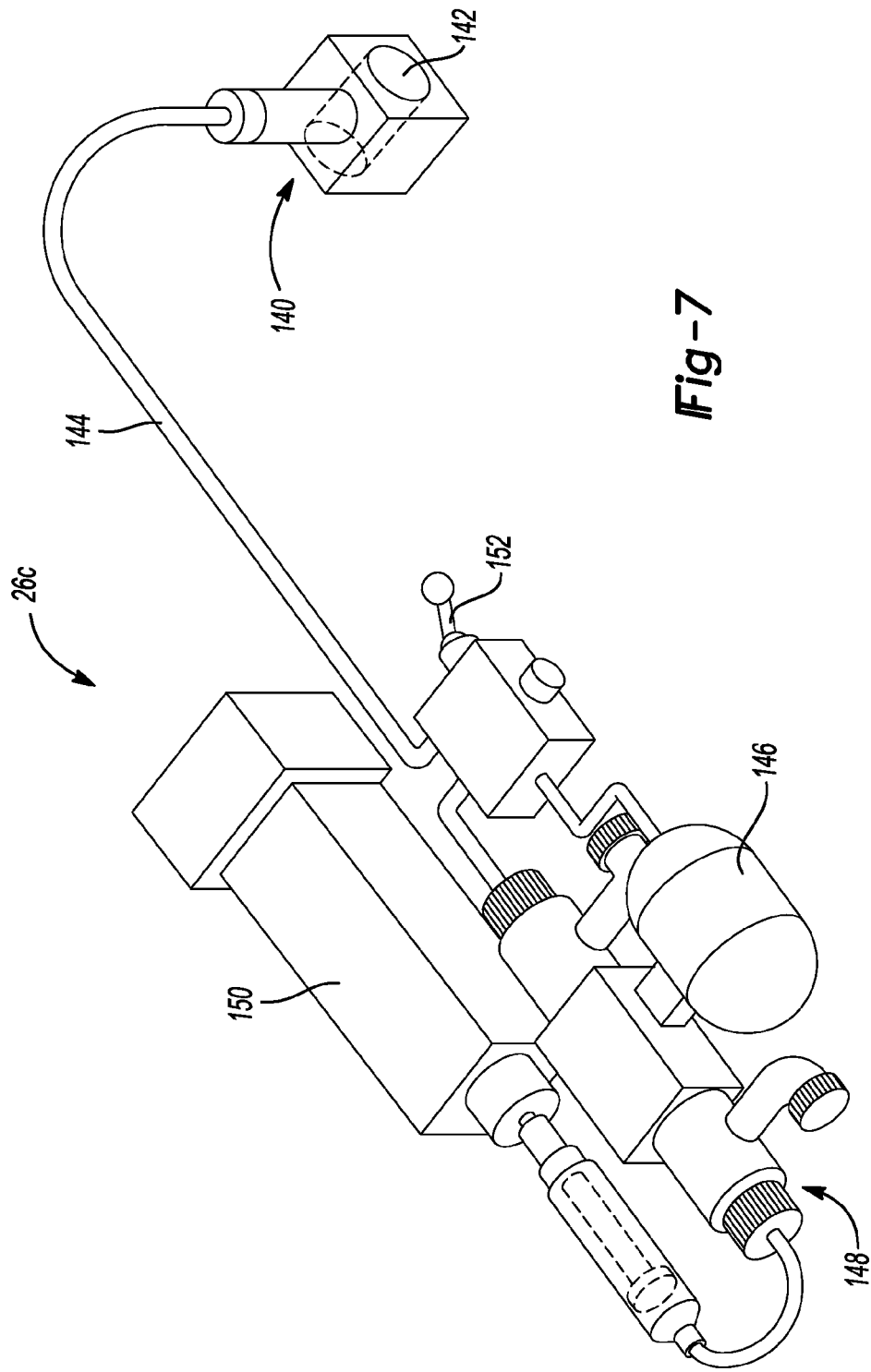
FIG. 7 is a partial assembled perspective view and schematic view of a stimulator system, according to various embodiments.

With reference to FIG. 7, a thumb stimulator 26c is schematically illustrated. The thumb stimulator assembly 26c can include a thumb holder housing 140 that includes a thumb hole 142 and a thumb pressure transducer pad 34, as discussed above. A hydraulic hose or connection 144 can connect the thumb holder housing 140 with a reservoir 146 of appropriate hydraulic fluid or gas. The reservoir 146 can be connected through a valve 148 with an actuator 150, of appropriate design, to drive or push the hydraulic fluid through the connection line 144 to move the transducer pad 34 within the thumb holder housing 140. Accordingly, in addition to the mechanical or motor system, including those discussed above, a hydraulic system, including that illustrated schematically in the thumb stimulator 26c, can be provided. A cut off or safety switch 152 can also be provided to substantially reduce or remove pressure or hydraulic fluid from the connection line 144 between the reservoir 146 and the thumb holder housing 140. It will be understood, that the thumb stimulator assembly 26c can also include the various communication and control systems discussed above according to the other various embodiments to control and communicate with the central processing 20 for receiving data regarding the test and sending an algorithm for operating the test on the patient.

Non-Digit Stimulation

The MAST system 18 present device can assess more than one sensory threshold in order to determine if an individual is only sensitive to a single sensory modality (suggesting a problem with that sensation) or more than one (suggesting a central nervous system derangement in function of all sensory systems). Furthermore, the MAST system 18 is also able to present more than one stimulus simultaneously, to allow the performance of sensory testing paradigms that require giving one stimulus while assessing the response to another (e.g., to test for the integrity of descending analgesic pathways).

In some embodiments, as illustrated in FIG. 1, the MAST system 18 can be configured for visual stimulation via wireless goggles 160. The goggles 160 may communicate with a wireless link 162 to the central processor 20, although a wired link may also be provided. Pressure stimulation to other areas of the body, including the forearms, legs, shoulders, vulva, anus or rectum, and head and neck regions, in addition to the thumbnail pressure actuator can also be used and connected to the central processor 20. For example, a larger opening may be provided in a device similar to the thumb stimulator 26 to receive the patient forearm. An auditory stimulator 170, such as headphones, can also be linked 172 with the central processor 20. Also, olfactory stimulators 173 can be provided to test olfactory response and linked to with the central processor 20 with a link 173a. An intra-oral "chewing pain" actuator 175 that is linked to the central processor 20 with a link 175a that operates from MAST system 18 can be used. In some embodiments, a radiological compatible version can be constructed using a remote motor and all plastic or shielded components to allow for pain testing to be conducted during functional magnetic resonance imaging (fMRI).

Applications

In some embodiments, a streamlined and simplified "clinical use only" version of this system would allow for QST to be conducted on patients during routine medical care. In such cases, an "on" button, such as the button 82, located on the hand piece 60 could commence one or more brief, preconfigured testing algorithms. Patient feedback (i.e., pain ratings) can be entered directly into the hand piece via the small control panel and/or buttons 82 located directly on the hand piece and would not require the use of additional input devices. The small LCD monitor 84 can also be located on the hand piece to display testing results to the clinician.

Thus, the MAST system 18 can be completely automated and have computer-controlled operation. For example, the patient may place his thumb 92, or other digit, in the stimulator 26 in the thumbhole 62 and to contact the digit placement site. The patient can then press the button 82 to indicate readiness to an operator to start the test procedure. The central processor 20 or the controller 74 can then access the program and apply a force to the transducer pad 34 according to the test procedure of the program. The subject can then provide feedback with the buttons 82 or the subject input panel 24. The input can be over time (e.g. with a scale to indicate increasing or decreasing pain) or to indicate a pain threshold has been reached. The input can be transmitted to the central processor 20 or the controller 74 for storage or analysis. The controller 74 can control the drive system according to the program and terminate stimulation according to the program. This automation can reduce or remove variability in application or force by the operator or the subject and remove bias of the operator or the subject during the test.

The MAST system 18, including the stimulator 26, can use a small or micro-electrical motor to produce force during the test. The motor can be small and portable with an included power cell in the portable device. Also, the MAST system 18 can create or receive input from multiple types of sensation delivered from the same device. Also, the stimulator 26 can have wireless control, be battery operated, and include an ergonomic hand piece with an integrated patient feedback system. Also, the stimulators can be designed for the ability for subjects to test themselves.

The central processor 20 can coordinate testing protocols and program execution in the MAST system 18. The testing procedure can also be overseen by an operator or run in "kiosk mode", where the patient can begin or end the testing procedure, but not manipulate any key test variables. Operators can custom configure the testing algorithm and monitor test progress in real-time and/or analyze results in real-time or after completion of the test program.

The force applied to the subject can be measured using a full-bridge strain gauge load cell as the force sensor 42. According to Newton's $3^{rd}$ law of motion, the transducer pad or plunger 34 exerts a force on the patient and the subject will exert and equal but opposite force on the plunger. This force will compress the plunger and this variation in strain is measured through minute changes in resistance of the sensing elements. These measured signals are used for feedback control of the force, position and speed applied by the plunger. The embedded PID control system incorporates linearized calibration curves to ensure accurate and repeatable testing can be performed. Additionally, the controller parameters can be tuned to customize the force stimulation profile providing added flexibility for research applications.

Figure 8:
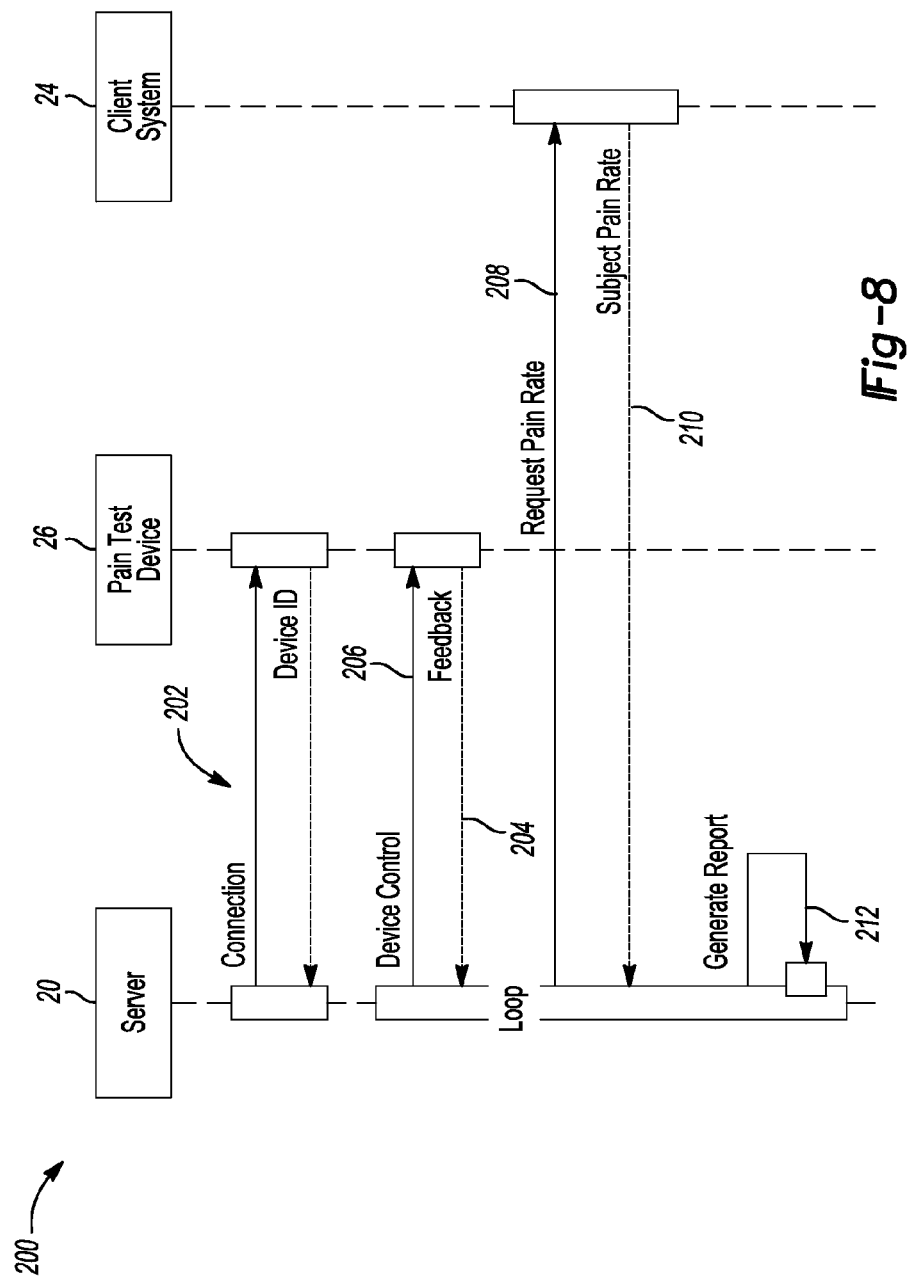
FIG. 8 is a diagram of connections of a system according to various embodiments.

According to an exemplary embodiment, and with reference to FIGS. 8 and 9, the MAST system 18 is illustrated schematically showing transmission of instructions and/or feedback (data/information) between the various components. The sequence diagram 200 shown in FIG. 8 shows the interaction among the MAST system 18. Generally, the sequence diagram 200 can be encoded in software to be executed by the various components. The server terminal, which can be the central processor 20, first pairs (e.g. with Bluetooth® compliant systems) or connects 202 to external devices, including the stimulator 26 and/or the subject input 24, in order to control the devices and/or receive information from the devices. Then, the stimulator 26 can be controlled via feed back 204 with the central processor 20, including sending instructions via transmission 206 regarding a designed experiment. The server/central processor 20 can then repeatedly request 208 client feedbacks 210 during the test. The client feedbacks can be the subject inputting perceived pain values, or discrete times periods such as onset of pain or onset of intolerable pain. When the test is finished, the server/central processor 20 can generate a test report 212 for the entire experiment.

It will be understood, that the experiment design can be saved in the memory 21. Also, the experiment design can be a user augmented design of a standard design saved in the memory 21. Moreover, once the server/central processor 20 has paired and sent the device control 206 the controller 74 of the stimulator 26 can control the rate of pressure application, test run time, etc., as discussed above. Thus, though the server/central processor 20 can send the test parameters, the stimulator controller 74 can run the test without further input. Thus, the server/central processor 20 can provide overall test series control, while the stimulator controller 74 controls discrete testing performance.

With reference to FIG. 9, the internal server/central processor 20 operation sequence is shown in a sequence diagram 250. Again, the operation sequence can be encoded in a computer program to be executed by the server/central processor 20 and based on inputs from a user and/or subject. The interactions illustrated in the sequence diagram 250 between the server application components are shown in sequential order from the top to the bottom and in the order that those interactions occur. The server application components include the server application 252, the server network configuration 254, the server experimental configuration 256, and the server test design 258.

Firstly the server application 252 requests available network resources 260 and initializes a backend server thread for potential TCP/IP connections 262 to configure communications within the server/central processor 20 and with the other devices 24, 26. Then the server application 252 requests experimental information 264 and collects experimental information 266 from the experimental information form. The experimental information can include experimenter identification, subject identification, etc. and can be input by the operator prior to or during the test. The server application 252 then requests test design tools 268 and uses the received test design tools to generate proper experiment signals 270. The test design tools can be the recalled test design regarding maximum force, rate, sound levels, etc. from the memory 21. The test design tools can also include any experimenter specific augmentations of predetermined test parameters. The signals can be those signals that are then sent to the various stimulators 26, etc. and can be sent via the connections 36, 40. After all the preparation steps, the server application 252 can process all the test signals to control the external devices 272, store (e.g. also to the memory 21) the received feedbacks from the client and updates the graphic charting periodically 274. Periodic charts can be viewed by the operator, such as on the display 22, for real time analysis or used by the server application 252 for real time analysis. When the test is ended, the server application 252 can generate a test report 276 using all the experiment data. The experiment data can include the patient feedback (e.g. regarding pain or any stimulated response of the subject) and the sensor feedback from the stimulator (e.g. force, pressure/strain, etc.). The test report can be printed, displayed for the operator/user on the display 22, stored to a network, etc.

In using the MAST system 18, safety of the patient can be provided with numerous software and hardware based failsafe systems. Firstly, for hardware based safety, the system can be designed to be incapable of producing a force greater than a selected amount, such as about 200 N. Secondly, a kill switch can be used to allow the power to the motor 68 or other drive system to be instantly removed. Thirdly, a mechanical knob can be directly connected to the plunger 34 and can be used to manually move the plunger 34 once the power to the motor 68 has been removed. Fourth, a maximum power the device can deliver to the motor operating in open-loop mode can also be set by placing a limit on the largest duty cycle allowed. This will prevent excessive forces occurring even if the loadcell fails. Embedded software safety systems in the controller 74 or the central processor can also include at least two adjustable force limits. The first will immediately end the stimulus application should excessive forces be detected. The second is set at a slightly higher force than the first and will remove power to the motor in the event the action taken by the first limit fails.

Additionally, the stimulus application can be controlled by the hand piece and not the central processor 20 or server, so that communication problems or disruption will not affect the resolution of the stimulus. Also, once the device is paired with the central processor 20, communications can be securely encrypted and various error detection algorithms used to ensure corrupted data will not be acknowledged by the device 26. This prevents malicious interference with a testing session from a third party or unexpected spurious behavior of the device 26 due to noise sources traditionally associated with wireless communications. Additionally, server based safety systems allow the operator (or subject in the "kiosk mode") to immediately terminate a test and any stimuli being applied at any moment.

In some embodiments, the pressure stimulator 26 can include software with the processor/controller 74 that can provide data analysis. In this way, the pressure stimulator 26 can provide output independent of another computer, such as the central processor 20, and even independent of an operator. For example, a result such as a value or diagnosis can be displayed on the LCD screen 84 on the device 26 and may be recorded into the subject's record by an operator, physician, or by the subject.

In some embodiments, the MAST system 18 provides a portable device for determining a subject's pain level at the thumbnail or other areas (e.g. head, face, legs). Also, additional or alternative stimulators can be used to measure or gauge a subject's response to non: pressure/strain stimuli (e.g. visual, olfactory, heat). In certain embodiments, the portable device is a hand-held apparatus; most preferably the apparatus employs an automated pressure member to deliver a blunt force stimulus to the subject's thumbnail bed. The device, and/or a system employing the device, records the level of stimulus and receives input from the subject based on the perceived level of pain.

Additionally, in accordance with some embodiments, the MAST system 18 allows for interfacing between the central processor 20 and the subject, as well as between the central processor 20 and the MAST system operator, to allow for input by the subject and/or the operator. Moreover, the central processor 20 can automatically acquire and record input from the interface between the subject and the central processor 20, or the interface between the central processor 20 and the MAST system operator, thereby facilitating the MAST system's 18 operability by a single person. In some cases, the central processor 20 can be contained within the portable pressure stimulator device 26.

The MAST system 18 and various embodiments of the stimulator 26 can be used in conjunction with other systems and devices, including those as described in Polianskis et al., European Journal of Pain (2001) 5: 267-277; Baguley et al., Physiol. Meas. 24 (2003) 833-836; force measurement instruments and gauges sold by Nidec-Shimpo Corp. having a place of business in Itasca, Ill.; pain test algometers sold by Wagner Instruments having a place of business in Greenwich, Conn.; Johnson et al., Anaesthesia (1997) 52, 1070-1072.

The embodiments and the examples described herein are exemplary and not intended to be limiting in describing the full scope of apparatus, systems, and methods of the present technology. Equivalent changes, modifications and variations of some embodiments, materials, compositions and methods can be made within the scope of the present technology, with substantially similar results.

What is claimed is:

1. A stimulator system for sensory testing of a subject by stimulating a portion of the subject and receiving feedback from the subject, comprising:
    a housing member having:
        a stimulation site having a surface within the housing member, the surface configured to be accessible through an aperture in the housing member, wherein the aperture is configured to allow the portion of the subject to access a passage in the housing member to position the portion of the subject on the surface;
        a transducer member associated with a drive system, wherein the transducer member is moveable by the drive system at least towards the surface of the stimulation site through a drive aperture in the housing member, wherein the transducer member is positioned to at least apply pressure on at least the portion of the subject and bias the portion of the subject against the surface of the stimulation site;
        a power source coupled to the drive system;
        a controller operably coupled to the drive system;
        a communication system coupled to the controller; and
    an input system for sending at least a user input signal including the feedback from the subject to the controller of a rating by the subject regarding at least the pressure applied on at least the portion of the subject by the transducer member.

2. The stimulator system of claim 1, further comprising:
    a display located on the housing member or remote from the housing member.

3. The stimulator system of claim 1, further comprising:
    a central processor operable to communicate with the controller on the housing member;
    wherein the central processor is operable to send a pressure stimulation signal via the communication system to automatically apply pressure to the portion of the subject according to a pre-determined procedure and the central processor is configured to receive subject feedback based on the automatically applied pressure.

4. The stimulator system of claim 3, further comprising:
    a memory system configured to store software incorporating the pre-determined procedure which includes at least one of rate and duration of application of force, peak force, incremental or continuous force application, inter-stimulus interval, or patient response scales.

5. The stimulator system of claim 3, further comprising:
    in addition to the transducer member, at least one of an auditory stimulator, an appendage stimulator, a chew stimulator, an olfactory stimulator, and a visual stimulator;
    wherein the least one of the auditory stimulator, the appendage stimulator, the chew stimulator, the olfactory stimulator, and the visual stimulator is operable to receive a further stimulation signal from the central processor to stimulate the subject in addition to or alternatively to the transducer member.

6. The stimulator system of claim 1, wherein the drive system comprises:
    an electric motor configured to be powered by the power source housed within the housing member; and
    a rack and pinion assembly configured to convert rotational movement of the electric motor to linear movement;
    wherein the transducer member is associated with the rack and pinion assembly.

7. The stimulator system of claim 1, wherein the communication system is configured to at least one of send or receive signals wirelessly.

8. The stimulator system of claim 1,
    wherein the stimulation site is configured to be accessible through the aperture and passage in the housing member by the portion of the subject when grasped by a hand of the subject.

9. A method of operating a sensory stimulation system and receiving a feedback from a subject regarding sensory stimulation, comprising:
    accessing and executing a stored program by at least one processor to transmit a stimulation signal to a stimulator system to apply a stimulus including a pressure to the subject based on instructions of the stored program;
    initiating operation of the stimulator system;
    operating the stimulator system, after the initiation of the stimulator system, automatically and based on the executed program and the stimulation signal transmitted to the stimulator system to apply a stimulus to the subject;
    receiving the feedback from the subject regarding the applied stimulus including pressure based on operation of the stimulator system regarding the applied stimulus, wherein the feedback from the subject includes a rating regarding the applied stimulus including pressure;
    receiving a feedback from the stimulator system regarding the applied stimulus;
    analyzing at least one of (i) the received feedback from the subject regarding the applied stimulus including pressure or (ii) the received feedback from the stimulator system;
    placing at least one digit of a hand of the subject on a digit placement site within a housing member; and
    applying the stimulus including the pressure to the at least one digit of the subject, including:
        moving a transducer member with a drive system, at least towards the digit placement site through a drive aperture in the housing member, wherein the transducer member is positioned to apply the pressure on at least a portion of the at least one digit and biasing the at least one digit against the digit placement site;
        receiving the stimulation signal with a receiver of the stimulator system from the at least one processor based on the executed instructions; and operating the drive system with a drive system controller based on the received stimulation signal.

10. The method of claim 9, further comprising:
providing a wireless communication system coupled to the stimulator system receiver to allow the stimulator system receiver to be configured to wirelessly receive the stimulation signal; and
executing instructions with the drive system controller based on the received stimulation signal to move the transducer member according to the stimulation signal.

11. The method of claim 10, further comprising:
inputting the feedback from the subject in response to the movement of the transducer member including the rating regarding the applied pressure.

12. The method of claim 11, wherein inputting the feedback from the subject includes inputting the time of the onset of pain.

13. The method of claim 10, further comprising:
sensing a force that is applied to the at least one digit with the transducer member;
sensing a strain resulting from deformation at a stimulation site; and
sending at least one of (i) a force signal based on the sensed force to the at least one processor or (ii) a strain signal based on the sensed strain to the at least one processor;
wherein applying the stimulus includes biasing the at least one digit against the digit placement site further includes biasing the at least one digit against a surface within the housing member.

14. The method of claim 13, further comprising:
providing at least a first processor of the at least one processor in the housing member; and
providing a user input system located on a surface of the housing member for inputting the feedback from the subject.

15. The method of claim 13, further comprising:
wherein sensing the strain is used for a feedback control of at least one of a force, a position, and a speed of the transducer member of the stimulator system;
wherein the drive system controller is configured to incorporate linearized calibration curves to ensure accurate and repeatable application of the stimulus to the subject based at least on the stimulation signal.

16. The method of claim 9, further comprising:
driving the transducer member with the drive system; and
applying the stimulus with driving the transducer member to the at least one digit;
wherein the stimulus is applied automatically according to the executed program.

17. The method of claim 9,
wherein applying the stimulus to the subject with the stimulator system further includes at least one of an auditory stimulus, a visual stimulus, and an olfactory stimulus.

18. The method of claim 9, further comprising:
monitoring strain at a stimulation location as a result of applying the stimulus that includes a pressure stimulus to the stimulation location of the subject;
wherein receiving feedback from the stimulator system regarding the applied stimulus includes monitoring an applied stress and monitoring the strain;
wherein receiving feedback from the subject based on operation of the stimulator system regarding the applied stimulus includes receiving a perceived stimulus response from the subject including a rating over time indicating at least an increasing or a decreasing pain; and
analyzing the received feedback from the stimulator system and the received feedback from the subject by executing instructions with the provided at least one processor to provide a report based on a test including applying the stimulus.

19. The method of claim 18, wherein initiating operation of the stimulator system includes using an on button located on a hand piece of the stimulator system;
wherein operating the stimulator system commences at least one preconfigured testing algorithm;
wherein receiving feedback from the subject is entering directly with the hand piece via a control panel or one or more buttons located directly on the hand piece without additional input devices.

20. The method of claim 18, wherein initiating operation of the stimulator system is performed by the subject;
wherein operating the stimulator system further includes a custom configured testing algorithm and an in real-time monitor testing progress or analyzing results in real-time.

21. The method of claim 9, wherein the rating regarding the applied pressure includes at least one of a time of an onset of pain, a rating over time of increasing or decreasing pain, or combinations thereof.

22. The method of claim 9, wherein analyzing the at least one received feedback includes displaying a value of the at least one feedback or a diagnosis based on the at least one received feedback.

23. A pressure stimulator system for sensory testing at least a digit of a human user and a feedback system from the human user, comprising:
a housing member configured to be held in a single hand of the human user while the digit is placed against a digit placement surface, wherein the housing member has an aperture through an exterior wall of the housing member configured to allow access to the digit placement surface by the digit of the single hand within the housing member;
a drive system operable to be powered with a power source, wherein both the drive system and the power source are within the housing member;
a transducer member coupled to the drive system, wherein the transducer member is moveable by the drive system at least towards the digit placement surface through a drive aperture in an internal wall of the housing member, wherein the transducer member is configured to apply pressure on at least a portion of the digit of the human user and bias the digit against the digit placement surface to apply a pressure to the digit with the transducer member;
a local controller to control the drive system; and
an input system for inputting a human user signal from the human user to relate a perception of the human user based on the applied pressure on at least the portion of the digit of the human user.

24. The pressure stimulator system of claim 23, further comprising:
a central processor and a central processor wireless communication system; and
a local controller wireless communication system;
wherein the central processor is configured to send or receive a signal from the local controller with the central processor wireless communication system and the local controller wireless communication system.

25. The pressure stimulator system of claim 24, further comprising:

a sensor to sense the amount of pressure or deformation applied to the digit;

wherein the signal is a stimulation signal regarding the sensed amount of pressure or deformation.

26. The pressure stimulator system of claim 25, wherein the drive system includes an electric motor and the power source is a battery;

wherein the electric motor drives a rack and pinion assembly that is configured to drive the transducer member.

27. The pressure stimulator system of claim 24, wherein the signal includes at least a first signal and a second signal;

wherein the first signal is a test procedure signal communicating a test procedure to the local controller for operating the drive system; and wherein the second signal is the human user input signal, wherein the second signal is operable to indicate at least one of an onset of pain in the human user or a rating of a pain over a time;

wherein at least one of the central processor or the local controller is configured to execute instructions to analyze a relationship of the test procedure signal and the human user input signal based on an applied stimulus with the transducer member.

* * * * *